United States Patent [19]

King

[11] 4,339,461

[45] Jul. 13, 1982

[54] N-SUBSTITUTED 3-NITRO-BENZYLAMINES

[75] Inventor: William F. King, Novato, Calif.

[73] Assignee: Chevron Research Company, San Francisco, Calif.

[21] Appl. No.: 221,169

[22] Filed: Dec. 29, 1980

[51] Int. Cl.$^3$ ............................................ A61K 31/135
[52] U.S. Cl. .................................... 424/330; 424/321; 564/99; 564/384
[58] Field of Search ................. 564/99, 384; 424/321, 424/330

[56] References Cited

U.S. PATENT DOCUMENTS 3,227,758  1/1966  Richter et al. ...................... 564/384
3,265,731  8/1966  Epstein ................................. 564/99

OTHER PUBLICATIONS

Jour. Amer. Chem. Soc., vol. 70 (1948), 1365.

*Primary Examiner*—Bernard Helfin
*Attorney, Agent, or Firm*—J. A. Buchanan, Jr.; T. G. DeJonghe; S. L. Biggs

[57] ABSTRACT

N-substituted-3-nitro-benzylamines have been found to be fungicidally effective, particularly against Tomato Early Blight and Bean Powdery Mildew.

10 Claims, No Drawings

N-SUBSTITUTED 3-NITRO-BENZYLAMINES

BACKGROUND OF THE INVENTION

Burkhalter et al disclose in *Journal of the American Chemical Society*, Vol. 70, pp. 1363 ff (1948), N,N-dipropyl-4-nitro-benzylamine, N,N-diethyl-3-nitro-benzylamine and N,N-diethyl-4-nitro-benzylamine as having antimalarial activity.

SUMMARY OF THE INVENTION

I have found that N,N-dipropyl-3-nitro-benzylamine and N-(3-substituted-phenyl)-3-nitro-benzylamines have unexpected fungicidal activity, particularly in the control of Tomato Early Blight, (*Alternaria solani*) and Bean Powdery Mildew (*Eronyces phaseoli*).

DESCRIPTION OF THE INVENTION

Compounds of the invention are of the formula:

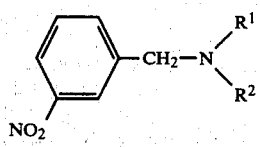

wherein $R^1$ and $R^2$ are both propyl or $R^1$ is the group

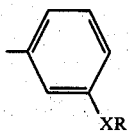

wherein X is S or $SO_2$ and R is alkyl of 1 to 4 carbon atoms; and $R^2$ is hydrogen or $-SO_2R$ wherein R is defined as hereinabove.

Preferably $R^1$ and $R^2$ are both propyl. When $R^1$ is a substituted phenyl group, preferably X is S and R is methyl.

The compound N,N-dipropyl-3-nitro-benzylamine and N-(3-substituted phenyl)-3-nitro-benzlamines have unexpected fungicidal activity since the type of substituent on the nitrogen atom is specific for activity as is the type and placement of the substituent on the phenyl ring of the benzyl group. The compounds in Table I below were tested according to procedures as shown in Examples 1 and 2.

TABLE I

Fungicidal Efficacy - % Control @ 250 ppm $$\text{Y}\diagdown\text{C}_6\text{H}_3(\text{X})-\text{CH}_2\text{N}(R^1)(R^2)$$

| No. | X | Y | $R^1$ | $R^2$ | TEB | BPM | TLB |
|---|---|---|---|---|---|---|---|
| 1 | H | $NO_2$ | $CH_2CH_2CH_3$ | $R^1$ | 60 | 86 | — |
| 2 | H | $NO_2$ | $CH_2CH_3$ | $R^1$ | 0 | 0 | — |
| 3 | $NO_2$ | H | $CH_2CH_2CH_3$ | $R^1$ | 0 | 0 | — |
| 4 | H | F | $CH_2CH_2CH_3$ | $R^1$ | 0 | 0 | — |
| 5 | H | $NO_2$ | $\text{C}_6\text{H}_4\text{-}SCH_3$ | H | — | 79 | — |
| 6 | H | $NO_2$ | $\text{C}_6\text{H}_4\text{-}SCH_3$ | $-SO_2CH_3$ | 81 | — | 75 |
| 7 | H | $NO_2$ | $\text{C}_6\text{H}_4\text{-}SO_2CH_3$ | H | — | — | 75 |

TEB = Tomato Early Blight
BPM = Bean Powdery Mildew
TLB = Tomato Late Blight

Comparison Compound No. 2 shows that when the N-alkyl substituent contains only 2 carbon atoms, there is no fungicidal activity on Tomato Early Blight and Bean Powdery Mildew. Comparison Compound No. 3 shows that when the nitro substituent is shifted to the para-position rather than the meta-position there is no fungicidal activity. Comparison Compound No. 4 shows that when a fluoro group is substituted for the nitro group there is no fungicidal activity. It is therefore surprising that the $C_3$ carbon chain on the nitrogen and the meta-nitro group on the phenyl ring is specific for activity.

Also, Compounds 5, 6 and 7 having 3-substituted phenyl substituents exhibit activity comparable to that of Compound 1.

The compounds of the invention are applied in fungicidally effective amounts to fungi and/or their habitats, such as vegetative hosts and nonvegetative hosts, e.g., animal products. The amount used will, of course, depend on several factors such as the host, the type of fungus and the particular compound of the invention. As with most pesticidal compounds, the fungicide of the invention is not usually applied full strength, but is generally incorporated with conventional, biologically inert extenders or carriers normally employed for facilitating dispersion of active fungicidal compounds, recognizing that the formulation and mode of application may affect the activity of the fungicide. Thus, the fungicide of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5-80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, for example: the aryl and alkylaryl sulfonates and their sodium salts, alkylamide sulfonates, including fatty methyl taurides; alkylaryl polyether alcohols, sulfated higher alcohols and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLE 1

Tomato Early and Late Blight

Compounds of Table I were tested for the control of the Tomato Early Blight organism, *Alternaria solani conidia*, and Tomato Late Blight, *Phytophthora infestans conidia*. Tomato (variety Bonny Best) seedlings of 6 to 7 weeks old were used. The tomato plants were sprayed with a 250 ppm solution of the test compound in an acetone-and-water solution containing a small amount of a nonionic emulsifier. The sprayed plants were inoculated one day later with the organism, dried and maintained at 60-80% relative humidity for about 12 days. Percent disease control was based on the percent disease development on untreated check plants. The compounds tested and the results are tabulated in Table I.

The test was repeated for Tomato Early Blight on Compound No. 1. At dosages of 100, 40 and 16 ppm, Compound No. 1 exhibited 93%, 90% and 90% control, respectively.

EXAMPLE 2

Powdery Mildew

The powdery mildew test was made using bean seedlings (variety Bountiful) with well-developed primary leaves. The pathogen was *Erysiphe polygoni*. The bean seedlings were sprayed with a 250 ppm solution of the test compound in an acetone-water mixture containing a nonionic emulsifier. The treated plants were inoculated one day after spray application of the test compound with the pathogen. The plants were then maintained in a greenhouse at a 60-80% relative humidity and at a temperature of 68°-70° F. The rate of infection on the leaves was made after about 10 days. The percent disease control provided by a given test compound was based on the disease reduction relative to untreated check plants. The results are reported in Table I.

The test was repeated on Compound No. 1. At dosages of 100, 40, and 16 ppm, Compound No. 1 exhibited 83%, 56%, and 0% control, respectively.

EXAMPLE 3

Preparation of N,N-Dipropyl-3-Nitro-Benzylamine

To a solution of 5.13 g of m-nitro-benzyl chloride in 100 ml benzene at 10° C. was added in small portions 6.2 g of dipropylamine over a period of 15 minutes. The reaction mixture was stirred and allowed to come to room temperature for 1.5 hours, and was then refluxed for 4 hours. Water was added to the solution and the organic layer was separated and collected. The organic layer was washed with water (3×100 ml), dried ($MgSO_4$) and stripped to leave a dark-red oil. The product (Compound No. 1) was chromatographed over silica gel (hexane: $CH_2Cl_2$; 1.0:0; 4:1), to yield the title product as a yellow-amber oil. Analysis: C: calculated, 66.08; found, 65.38. H: calculated, 8.53; found 8.55. N: calculated, 11.85; found, 11.73.

EXAMPLE 4

Preparation of N-(3'-methylthiophenyl)-3-nitro-benzylamine

The procedure of Example 3 is followed employing m-methylthioaniline in place of dipropylamine to yield the title product (Compound No. 5).

EXAMPLE 5

Preparation of
N-(3-nitrobenzyl)-N-(3'-methylthiophenyl)-methane sulfonamide

The product of Example 4 is treated with methane sulfonyl chloride according to known procedures to yield the title product (Compound No. 6).

What is claimed is:

1. A compound of the formula

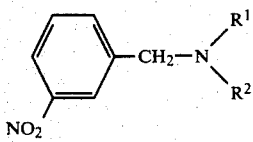

wherein $R^1$ and $R^2$ are both propyl or $R^1$ is the group

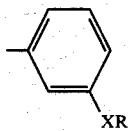

wherein X is —S— or —SO$_2$— and R is alkyl of 1 to 4 carbon atoms; and $R^2$ is hydrogen or —SO$_2$R wherein R is defined as hereinabove, provided that when X is —S—, $R^2$ is not hydrogen.

2. A compound according to claim 1 wherein $R^1$ is the group

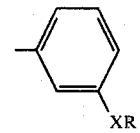

and $R^2$ is hydrogen or —SO$_2$R wherein R is alkyl of 1 to 4 carbon atoms.

3. A compound according to claim 2 wherein R is methyl and X is —S—.

4. The compound according to claim 1 wherein $R^1$ and $R^2$ are both propyl.

5. A fungicidal composition comprising a biologically inert carrier and a fungicidally effective amount of a compound defined in claim 1.

6. A method for controlling fungi comprising contacting said fungi or their growth habitat with a fungicidally effective amount of a compound defined in claim 1.

7. A method of controlling Tomato Early Blight fungi comprising contacting said fungi or their growth habitat with a fungicidally effective amount of a compound defined in claim 1.

8. A method of controlling Tomato Early Blight fungi comprising contacting said fungi or their growth habitat with a fungicidally effective amount of the compound defined in claim 4.

9. A method of controlling Bean Powdery Mildew fungi comprising contacting said fungi or their growth habitat with a fungicidally effective amount of a compound defined in claim 1.

10. A method of controlling Bean Powdery Mildew fungi comprising contacting said fungi or their growth habitat with a fungicidally effective amount of the compound defined in claim 4.

* * * * *